US005760034A

United States Patent [19]

Blythin

[11] Patent Number: 5,760,034
[45] Date of Patent: Jun. 2, 1998

[54] HETEROCYCLIC SUBSTITUTED NAPHTHYRIDINONES AND METHODS AND COMPOSITIONS EMPLOYING THEM

[75] Inventor: David J. Blythin, North Caldwell, N.J.

[73] Assignee: Schering Corporation, Kenilworth, N.J.

[21] Appl. No.: 852,214

[22] PCT Filed: Nov. 30, 1990

[86] PCT No.: PCT/US90/06873

§ 371 Date: May 29, 1992

§ 102(e) Date: May 29, 1992

[87] PCT Pub. No.: WO91/08208

PCT Pub. Date: Jun. 13, 1991

[51] Int. Cl.$^6$ .................. A61K 31/44; A61K 31/535; C07D 471/04
[52] U.S. Cl. .................. 514/234.5; 514/212; 514/300; 540/597; 544/427; 546/122
[58] Field of Search .................. 540/597; 544/127; 546/122; 514/212, 234.5, 300

[56] References Cited

U.S. PATENT DOCUMENTS

| | | |
|---|---|---|
| 4,596,809 | 6/1986 | Sherlock . |
| 4,684,727 | 8/1987 | Blythin et al. . |
| 4,786,642 | 11/1988 | Teulon . |
| 4,794,116 | 12/1988 | Blythin .................. 546/122 |

FOREIGN PATENT DOCUMENTS

| | | |
|---|---|---|
| 0231709 | 8/1987 | European Pat. Off. . |
| 0267691 | 5/1988 | European Pat. Off. . |
| 2567520 | 1/1986 | France . |
| WO89/00571 | 1/1989 | WIPO . |

OTHER PUBLICATIONS

Chemical Abstract, vol. 105: 208847a for FR. 2,567,520 (1986).

Derwent Abstract, 87–222774/32 for EP 231709.

Teulon, *Chemical Abstracts*, vol. 105:2 088479 (1986).

*Primary Examiner*—Robert W. Ramsuer
*Attorney, Agent, or Firm*—Henry C. Jeanette

[57] ABSTRACT

Nitrogen-containing heterocyclic substituted naphthyridinones and methods and compositions employing such compounds are disclosed.

9 Claims, No Drawings

HETEROCYCLIC SUBSTITUTED NAPHTHYRIDINONES AND METHODS AND COMPOSITIONS EMPLOYING THEM

BACKGROUND OF THE INVENTION

The present invention relates to certain heterocyclic substituted naphthyridinones and to methods and compositions using such compounds.

European published application No. 0 231 709 discloses phenyl naphthyridinones of the formula:

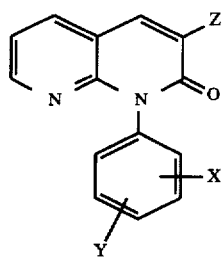

wherein Z is, for example, an amine functional group and X and Y are, for example, H, a halogen atom, a lower alkyl group, a trifluoromethyl, an alkoxy, a methylthio, a nitro or a cyano. Among the amine functional groups described are

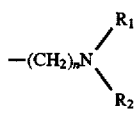

where n is 0 to 5 and it is possible for $R_1$ and $R_2$ to form a piperazine ring substituted by an alkyl or an aromatic nucleus which may or may not be substituted, or alternatively to form an imidazole ring. These compounds are disclosed as ulcer-inhibiting drugs.

U.S. Pat. No. 4,684,727 discloses zwitterionic bicyclic compounds of the formula:

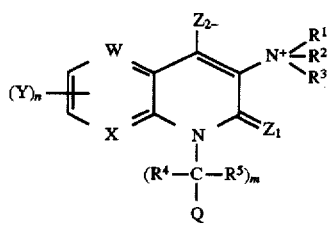

wherein the substitutents can be among those exemplified below:

W and X may be the same or different and each independently represents —CH= or —N=;

$Z_1$ and $Z_2$ are the same or different and each independently represents —O— or —S—;

$R^1$, $R^2$, $R^3$, $R^4$ and $R^5$ are the same or different and each may be independently selected from the group consisting of, for example, H, alkyl having from 1 to 12 carbon atoms, alkenyl having from 3 to 8 carbon atoms, alkynyl having from 3 to 8 carbon atoms, etc.;

in addition, two of $R^1$, $R^2$ and $R^3$ can be joined together to represent a ring which can contain from 2 to 8 carbon atoms, such as a pyrrole, piperidine or morpholine ring;

m is an integer of from 0 to 3;

n is an integer of from 0 to 2;

Q represents an aryl or an aromatic heterocyclic group which can optionally be substituted with 1 to 3 substituents Y; and each Y substituent is independently selected from the group consisting of, for example, hydroxy, alkyl having from 1 to 6 carbon atoms, halogen, $NO_2$, alkoxy having from 1 to 6 carbon atoms trifluoromethyl, cyano, etc. These compounds are disclosed as being anti-allergic, anti-inflammatory and/or cytoprotective agents.

SUMMARY OF THE INVENTION

We have now surprisingly found that compounds having the structural formula I

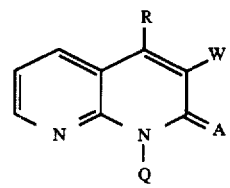

or a pharmaceutically acceptable salt thereof have activity useful in the treatment of allergy, inflammation, hyperproliferative skin disease and peptic ulcers, wherein:

R is H or alkyl;

A is O or S;

W represents

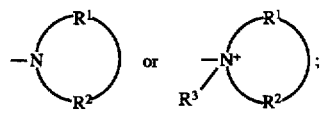

$R^1$ represents alkanediyl;

$R^2$ represents a covalent bond or -alkanediyl-O—;

$R^3$ represents alkyl, cycloalkyl, benzyl, substituted benzyl or hydroxyalkyl having 2 to 6 carbon atoms between the N atom and the OH group;

Q represents phenyl, 1- or 2-naphthyl, 1-, 2-, 3-, 4-, 5-, 6- or 7-indenyl or 1-, 2-, 3-, 4-, 5-, 6- or 7-indanyl, each of which may optionally be substituted with 1 to 3 Y groups as defined below; and each Y is independently selected from alkyl, halo, nitro, alkoxy, alkylthio, —$CF_3$, —CN, cycloalkyl, alkylsulfinyl or alkylsulfonyl.

Preferably, W is the group

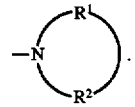

A is preferably O and Q is preferably phenyl or substituted phenyl. W is preferably

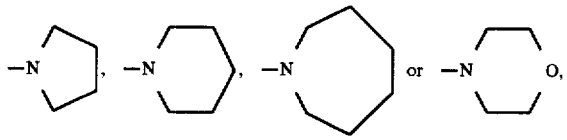

more preferably

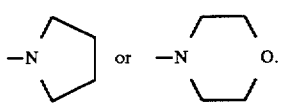

Particularly preferred compounds include:

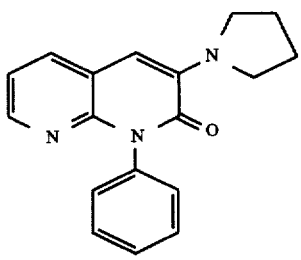

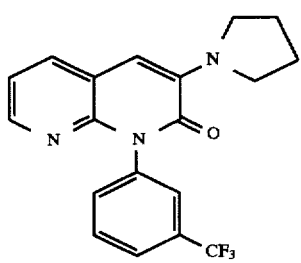

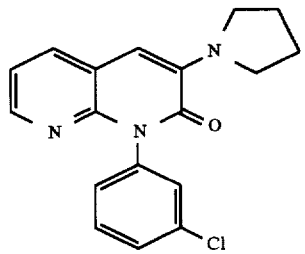

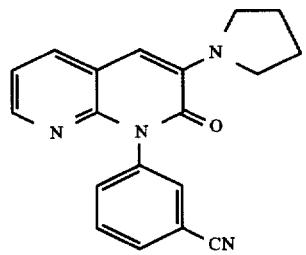

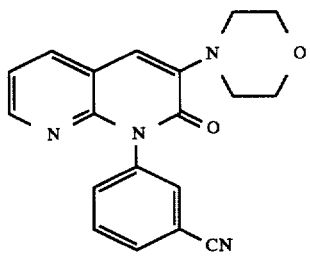

-continued

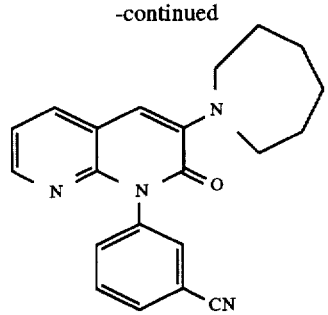

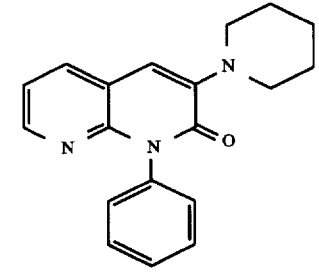

or

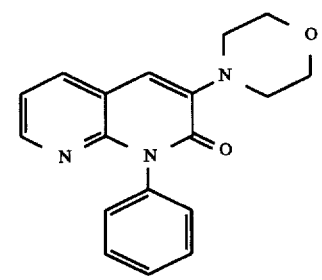

or a pharmaceutically acceptable salt thereof.

Other aspects of the invention involve a pharmaceutical composition comprising a compound of formula I above in combination with a pharmaceutically acceptable carrier and methods of treating allergic reactions, inflammation, inflammatory bowel disease, peptic ulcers and hyperproliferative skin disease in a mammal comprising administering to said mammal an effective amount of a compound of formula I for such purpose.

DETAILED DESCRIPTION OF THE INVENTION

Certain compounds of this invention may exist in isomeric forms. The invention contemplates all such isomers both in pure form and in admixture, including racemic mixtures.

Certain compounds of the invention of formula I can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of the invention.

Certain compounds of the invention e.g., those with a strongly basic amine group, also form pharmaceutically acceptable salts with organic and inorganic acids. Examples of suitable acids for such salt formation are hydrochloric, sulfuric, phosphoric, acetic, citric, oxalic malonic, salicylic, malic, fumaric, succinic, ascorbic, maleic, methanesulfonic and other mineral, sulfonic and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of this invention.

The following terms used in the present specification and claims have the meanings given below, unless otherwise indicated:

alkyl (including the alkyl portions of hydroxyalkyl, alkoxy, alkylthio, alkylsulfinyl and alkylsulfonyl)—represents a straight or branched, saturated hydrocarbon chain having from 1 to 10, preferably from 1 to 6, carbon atoms;

alkanediyl—represents a divalent, saturated straight or branched hydrocarbon chain, having from 1 to 10, preferably from 1 to 6, carbon atoms;

cycloalkyl—represents a saturated carbocyclic ring having from 3 to 10, preferably from 3 to 6 carbon atoms;

halo—represents fluoro, chloro, bromo or iodo;

substituted phenyl (including the substituted phenyl portion of substituted benzyl)—represents a phenyl group in which 1 to 3 hydrogen atoms thereof are replaced by the same or different substituents independently chosen from alkyl, halo, nitro, alkoxy, alkylthio, —$CF_3$, —CN, cycloalkyl, alkylsulfinyl or alkylsulfonyl; and substituted benzyl—represents a benzyl group in which the phenyl ring is substituted as defined above.

The compounds of the invention can be made by the processes described below with reference to Scheme 1:

In Step A, when $R^4$ is alkyl (preferably not methyl), the compound $QNH_2$ can be reacted in excess (preferably more than 2 equivalents) with the compound of Formula II and heated, preferably to about 125° C., for a time sufficient to provide the desired reaction, e.g. by following the reaction with thin layer chromatography. This reaction can be run neat or in a suitable solvent such as toluene, xylene, etc.

If $R^4$ in Formula III is H, it is preferably converted to an ester (i.e., $R^4$ is alkyl) by reaction under standard esterification conditions with, for example, potassium carbonate and diethyl sulfate in dimethylformamide.

In Step B, the ester of Formula III is reduced with a suitable reducing agent such as lithium aluminum hydride, lithium borohydride or lithium triethylborohydride ("Super Hydride®"). With "Super Hydride®", the reaction is preferably cooled, e.g., to a temperature of from about −20° C. to about room temperature. With lithium aluminum hydride, the reaction is normally performed in an ether such as diethylether under reflux. With lithium borohydride, the reaction is run initially at room temperature, then heated at reflux (e.g., in tetrahydrofuran) until the reaction is complete, e.g., as shown by thin layer chromatography.

The compound of Formula IV is oxidized in Step C with a suitable oxidizing agent such as activated manganese dioxide in a suitable solvent, such as benzene, toluene, xylene, chloroform, etc., at elevated temperature (e.g., about 50° C. to about 120° C.), preferably with removal of water formed in the reaction.

In Step D, the compound of Formula V is reacted with a compound of the Formula W—$CH_2$—$CO_2$alkyl in the presence of a catalytic amount of a suitable base. Exemplary bases include potassium t-butoxide, sodium ethoxide, etc. The reaction can be performed in a suitable solvent such as tetrahydrofuran (preferably containing a small quantity of a protic solvent such as t-butanol) or an alcohol solvent, preferably corresponding to the alcohol portion of the ester W—$CH_2$—$CO_2$alkyl. Other possible solvents include ether

SCHEME 1

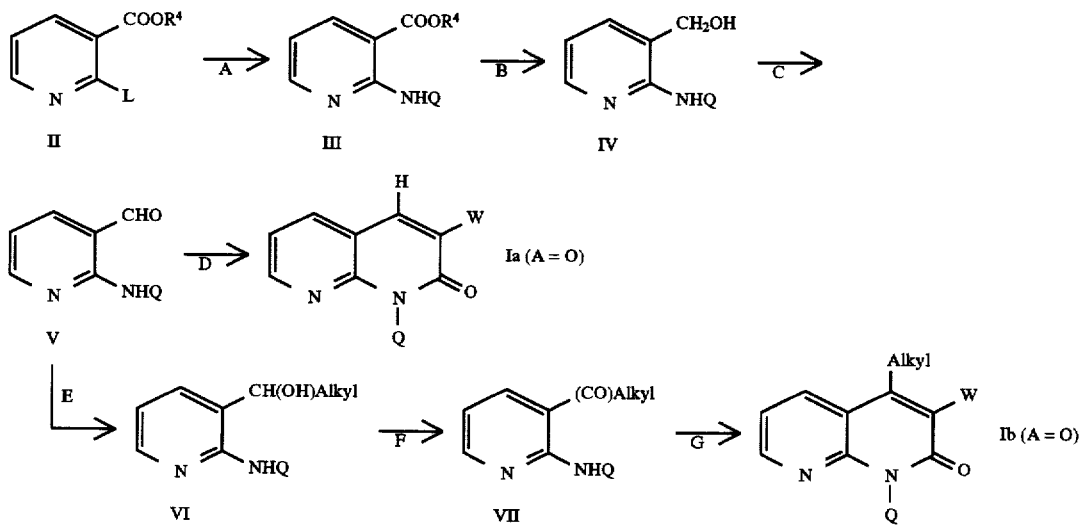

In the compound of Formula II, L represents a conventional leaving group such as chloro, bromo, iodo, tosyl, mesyl, etc. and $R^4$ can be H or alkyl. In Step A, the compound of Formula II wherein $R^4$ is H can be reacted with an amine of Formula $QNH_2$ in aqueous solution with an acid catalyst such as para-toluene sulfonic acid.

type solvents such as dioxane, dimethoxyethane, etc. The reaction can be run at any suitable temperature, preferably at room temperature or below.

In Step E, the compound of Formula V is reacted with a suitable alkyl organometallic agent MAlkyl, wherein M is, for example, a magnesium halide or lithium. This reaction is run in a suitable solvent such as an ether, e.g., diethylether or tetrahydrofuran. The reaction is preferably run at or below room temperature, e.g. from about 25° C. to about −20° C. The reaction is neutralized with a mineral acid to provide the compound of Formula VI.

The conditions and reactants for Steps F and G are essentially the same as those set forth above for Steps C and D, respectively.

The compounds of this invention wherein A is sulfur may be obtained by treating the purified 2-carbonyl compound of formula I with thiating reagents well known in the art. Lawesson's Reagent {2,4-bis(4-methoxyphenyl-1,3-dithia-2,4-diphosphetane-2,4-disulfide} or one of its analogues, in toluene, or phosphorus pentasulfide in pyridine are suitable for this purpose.

The compounds of formula I wherein W represents

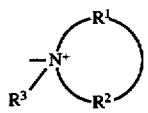

can be prepared by reacting a compound of formula I wherein W represents

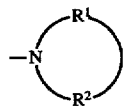

with a compound $R^3$ L wherein L represents a suitable leaving group such as chloro, bromo, iodo, tosyl, mesyl, etc. The reaction is carried out in an inert solvent such as toluene or xylene at elevated temperatures, e.g. from about 50° C. to about 140° C.

The compounds of this invention may be employed as anti-allergy agents in the treatment of, for example, asthma, allergic or seasonal rhinitis, and/or chronic bronchitis. The anti-allergy method of this invention is identified by tests which measure a compound's ability to inhibit leukotriene release.

In one such test procedure, the anti-allergy method of this invention is identified by tests which measure a compound's inhibition of leukotriene release in sensitized guinea pigs. Male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weigh 450–500 g. Sensitized guinea pigs are killed by a blow to the head and the lungs removed and cleaned of visible connective tissue, trachea and large blood vessels. The lungs from individual animals are sliced into fragments approximately 1 mm in thickness using a McIlwain tissue chopper and then washed with oxygenated Tyrode's buffer. Weighed aliquots (approximately 400 mg wet weight) of lung are transferred into vials containing 2 ml of fresh Tyrode's solution (containing 10 mM cysteine) and incubated in the presence or absence of test compound for 12 min at 37° C. The tissues are then challenged with 20 µg ovalbumin/ml (final concentration) and incubated for 15 min.

To measure leukotriene release, an aliquot of supernatant fluid is extracted with 4 volumes of 100% ethanol. After removal of the precipitated protein, the leukotriene content is measured by a radioimmunoassay using [$^3$H]LTC$_4$ and antiserum obtained from New England Nuclear. The cross-reactivity of the antiserum for LTD$_4$ is 55%. Percent inhibition of leukotriene release is calculated by comparing for each lung the release in the presence of the test compound to that in the absence of test compound. Representative compounds of the invention at a dose of 10 µM are found to inhibit leukotriene release in the test procedure as indicated below in Table 1:

TABLE 1

| Q | W | Inhibition of SRS-A release in vitro -Guinea Pig Lung 10 µM |
|---|---|---|
| phenyl |  | 34% |
| m-CF$_3$-phenyl |  | 46% |
| m-CN phenyl | 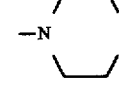 | 43% |
| phenyl | 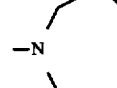 | 65% |
| m-CN-phenyl | 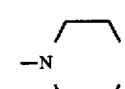 | 66% |
| m-CN-phenyl | | 46% |

The anti-allergy activity of the compounds of the invention may also be demonstrated by the following protocol:

Male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weigh 450–500 g. The sensitized guinea pigs are fasted overnight and the following morning are anesthetized with 0.9 ml/kg i.p. of dialurethane (0.1 g/ml diallylbarbituric acid, 0.4 g/ml ethylurea and 0.4 g/ml urethane). The trachea are cannulated and the animals are ventilated by a Harvard® rodent respirator at 50 strokes/minute with a stroke volume of 5 ml. A side arm to the tracheal cannula is connected to a pressure transducer (Harvard) to obtain a continuous measure of intratracheal pressure which is recorded on a polygraph (Harvard). The jugular vein is cannulated for the i.v. administration of substances. The sensitized guinea pigs are injected i.v. with 1 mg/kg propranolol, 5 mg/kg indomethacin and 2 mg/kg mepyramine given together in a volume of 1 ml/kg. The animals are challenged with antigen (0.5% ovalbumin) as an aerosol generated from a DeVilbiss® Model 65 ultrasonic nebulizer and delivered through the tracheal cannula for 30 seconds. Bronchoconstriction is measured as the peak increase in intratracheal pressure occurring within 15 minutes after antigen challenge.

Test compounds are administered orally 2 hours before challenge with ovalbumin. Suppression of anaphylactic bronchospasm is expressed as a percent inhibition of the peak increase in intratracheal pressure by comparison to a vehicle-treated control group.

Results from the above procedure for two compounds of the invention are listed in Table 2 below.

TABLE 2

| | | Inhibition of anaphylactic bronchospasm | |
|---|---|---|---|
| Q | W | Dose mg/kg | % Inhibition |
| phenyl | 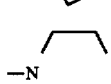 —N⟨pyrrolidine⟩ | 5 | 61 |
| phenyl | —N⟨morpholine⟩ | 5 | 93 |

The compounds of this invention are also useful for the treatment of inflammation. Thus, they are useful in the treatment of arthritis, bursitis, tendonitis, gout and other physical conditions characterized by inflammation. The anti-inflammatory use of the compounds of this invention may be demonstrated by the Reversed Passive Arthus Response Technique, as described below.

Reversed Passive Arthus Response (RPAR) Animals, Materials and Methods

Male Lewis inbred albino rats weighing 180–200 grams obtained from Charles River Breeding Laboratories are used in these experiments. The rats are housed 3 animals/cage and food and water are allowed ad libitum. The animals are numbered 1–3 in each cage and color marked for identification purposes.

Drug and Reagent Preparation

All reagents and drugs are prepared just prior to the study. Crystallized and lyophilized bovine serum albumin (BSA), available from Sigma Chemical Company, is solubilized without shaking in cold, sterile, pyrogen-free saline (10 mg/ml). Lyophilized anti-bovine serum albumin (IgG fraction), obtained from Cappel Laboratories, is suspended in sterile distilled water and diluted with cold, pyrogen-free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with an homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared and diluted so as to provide a dose for a 200 gram animal which is equivalent to the mg/kg dose for each experiment. Thus each rat receives an oral dose in a volume of approximately 2.0 cc. One hour after the last dose the animals are lightly anesthetized with ether and "sensitized" by injection of 0.2 ml of PFS containing 1.0 mg of BSA into the penile vein. One hour later, the animals are "challenged" in the right rear paw with subplantar injections of 0.2 ml of ml of PFS containing 0.1 mg of anti-BSA. Immediately after the subplantar injection, the right paw is dipped (up to the lateral malleolus) into the mercury well of a plethysmograph. The volume of mercury displaced is converted to weight and recorded. This value is considered to be the control reading for the animal. Paw volumes are subsequently recorded with a plethysmograph during the development of the inflammation at 2 and 4 hours post-challenge.

Results

Results are expressed by the change in paw volume (Δ paw volume) from the control reading for each animal to that recorded 2 and 4 hours post-challenge. All drug treated groups are compared to the MC control for significant differences with an analysis of variance.

The compounds of this invention are also useful in the treatment of peptic ulcers and stress ulceration, and to promote healing of gastric and/or duodenal ulcers. The antiulcer activity of the compounds of this invention is identified by standard tests which measure the cytoprotective effect in rats, e.g., by inducing gastrointestinal damage with ethanol prior to administering a compound of the invention. The compounds may be used as conjunctive therapeutic agents for coadministration with such anti-inflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents The compounds of formula I are useful in the treatment of hyperproliferative skin disease, e.g., psoriasis, which utility may be demonstrated by the Arachidonic Acid Mouse Ear Test as described below.

Arachidonic Acid Mouse Ear Test. Materials and Methods

Charles River, female, CD, (SD) BR mice, 6 weeks old, are caged 8/groups and allowed to acclimate 1–3 weeks prior to use.

Arachidonic acid (AA) is dissolved in reagent grade acetone (2 mg/0.01 ml) and stored at −20° C. for a maximum of 1 week prior to use. Inflammatory reactions are induced by applying 10 μl of AA to both surfaces of one ear (4 mg total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol.* 82, pp. 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

The activity against inflammatory bowel disease of the compounds of the invention can be demonstrated by the protocols described in G. P. Morris, L. Rebeiro, M. M. Herridge, M. Szewczuk, and W. Eepew, *Gastroenterology*, 86, 1188 (1984) and J. L. Wallace, *Can. J. Physiol. Pharmacol.*, 66, 422 (1988).

Administration of the dose can be intravenous, intranasal, parenteral, oral, subcutaneous, intramuscular, topical, transdermal or any other acceptable method. The compounds of the present invention can be administered in any number of conventional dosage forms. Solid dosage forms include capsules, tablets, pills, powders, suspensions, solutions, cachets or suppositories. Parenteral preparations include sterile solutions or suspensions. Inhalation administration can be in the form of a nasal or oral spray, or by insufflation. Topical dosage forms can be creams, ointments, lotions, transdermal devices (e.g., of the conventional reservoir or matrix patch type) and the like.

The formulations and pharmaceutical compositions contemplated by the above dosage forms can be prepared with conventional pharmaceutically acceptable excipients and additives, using conventional techniques. Such pharmaceutically acceptable excipients and additives include carriers, binders, flavorings, buffers, thickeners, color agents, dispersing agents, suspending agents, perfumes, preservatives, lubricants, etc.

When used orally or parenterally for the treatment of allergy, inflammation, peptic ulcers and/or hyperproliferative skin diseases, the compounds of the invention can be administered in an amount ranging from about 0.1 mg/kg body weight to about 25 mg/kg body weight, preferably from about 0.1 mg/kg body weight to about 5 mg/kg body weight per day. A typical recommended dosage regimen is oral administration of from 10 mg/day to 1500 mg/day, preferably from 10 mg/day to 250 mg/day, in two to four divided doses to achieve relief of the symptoms of inflammation.

Determination of the proper dosage of a compound of the invention for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition and size of the patient as well as severity of the symptom being treated.

The invention disclosed herein is exemplified by the following examples, which should not be construed to limit the scope of the disclosure. Alternative mechanistic pathways and analogous structures within the scope of the invention may be apparent to those skilled in the art.

PREPARATIVE EXAMPLE 1

Preparation of 2-(3-cyanophenylamino-3-pyridinemethanol

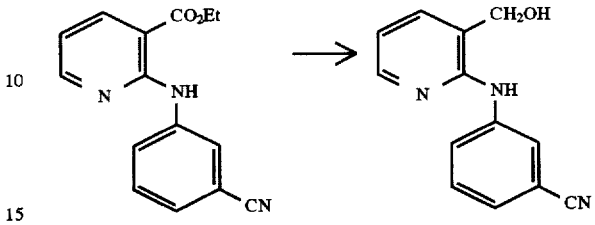

A 1 L 3-neck flask was equipped with an addition funnel with a glass stopper, a reflux condenser closed with a drying tube, and a dry $N_2$ inlet. An excess of $LiBH_4$ (3 g) was added to dry tetrahydrofuran (THF; 35 mL) contained in the flask. The mixture was stirred magnetically. Ethyl 2-(3-cyanophenyl)aminonicotinate (30 g) was dissolved in dry THF (250 mL) in the dropping funnel, and then this solution was added dropwise to the solution in the flask. After all had been added, the mixture was heated gradually to the reflux point (ca. 70° C). After heating at reflux for 2 h an additional 1.0 g of reducing agent was added, and later, a further 0.5 g. The reaction was followed by TLC until all the starting material had disappeared. The reaction mixture was then allowed to cool and was stirred at room temperature overnight. Solvent was removed under vacuum, and the product was poured over ice. The pH of the solution was adjusted to ca. 2 and it was allowed to stand for 3 h. The product was then extracted into ethyl acetate (3×200 mL). The combined ethyl acetate layers were washed with water (2×300 mL) then with saturated NaCl solution (2×250 mL). The separated organic layer was dried ($Na_2SO_4$), filtered and evaporated. The crude product was recrystallized from isopropanol to yield the desired product 18.9 g (75%), mp 132°–133° C. Found, C, 69.23; H, 5.06; N, 18.72. Calcd. (for $C_{13}H_{11}N_3O$), C, 69.32; H, 4.92; N, 18.66.

PREPARATIVE EXAMPLE 2

Preparation of 2-(3-trifluoromethylphenyl)amino-3-pyridinemethanol

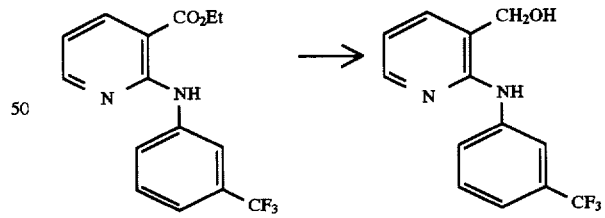

In a 3-neck 1 L flask, equipped with a reflux condenser closed by a drying tube, a dropping funnel with a septum cap on top, and a dry $N_2$ inlet, was placed ethyl 2-(3-trifluoromethylphenyl)aminonicotinate (30 g) and dry tetrahydrofuran (THF) (150 mL). The solution was stirred magnetically in an ice-salt bath for 20 minutes after which time the inside temperature had reached about −50° C. A solution of Super Hydride™ (lithium triethylborohydride; 250 mL of a 1M solution in THF) was transferred in the absence of air, using a double-ended needle, into the dropping funnel. This solution was added to the flask dropwise, keeping the temperature around 0° C. After all had been added the reaction mixture was allowed to warm to room temperature and was stirred overnight. Thin layer chromatography was used to follow the course of the reaction. Reaction was completed by the addition of a further 100 mL of the Super-Hydride™ solution at room temperature. The total product was poured over ice (400 g), with stirring, and the pH was adjusted to 5 with conc. HCl. Solid NaCl was added to salt out the organic layer which was separated. The aqueous layer was extracted with ethyl acetate (2×100 mL) and the organic layers were combined. The combined organic layer was washed with saturated NaCl solution (2×100 mL), dried (Na$_2$SO$_4$), filtered, and evaporated to a yellow oil. A small quantity of this crude product was purified by flash chromatography over silica gel eluting with hexane:ethyl acetate (80:20→67:33). Fractions containing the desired product were combined and evaporated to a light yellow solid, mp 105.5°–107° C. Found, C, 58.26; H, 4.24; N, 10.17. Calcd. (for C$_{13}$H$_{11}$N$_2$OF$_3$), C, 58.21; H, 4.13; N, 10.44.

PREPARATIVE EXAMPLE 3

Preparation of 2-(3-cyanophenyl)amino-3-pyridinecarboxaldehyde

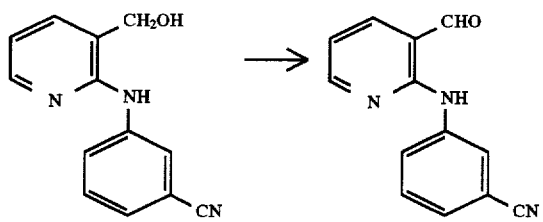

2-(3-trifluoromethylphenyl)amino-3-pyridinemethanol (1 g) was dissolved in toluene (50 mL) contained in a flask. The flask was attached to a Dean and Stark water-separator and a reflux condenser. To the reaction flask was added activated MnO$_2$ (4 g) and it was heated, with magnetic stirring, to about 80° C. The reaction was followed by thin layer chromatography and was complete after about 1.5 h. The product was filtered through a bed of celite which was washed with fresh ethyl acetate. The clear solution was evaporated to a yellow solid. The crude product was purified by running it through a flash column of silica gel, eluting with CH$_2$Cl$_2$:ethyl acetate (90:10) to yield the desired product, 0.56 g (57%), m.p. 152°–154° C. Found, C, 69.58; H, 3.90; N, 18.96. Calcd. (for C$_{13}$H$_9$N$_3$O), C, 69.94; H, 4.06; N, 18.83.

By essentially the same procedures described in Preparative Examples 1, 2 and/or 3 above, the compounds listed below were also prepared:

2-(3-trifluoromethyl phenyl) amino-3-pyridinecarboxaldehyde, mp 75°–77.5° C.; and
2-phenylamino-3-pyridinecarboxaldehyde.

Example 1

Preparation of 3-(1-pyrrolidinyl)-1-phenyl-1,8-naphthyridin-2(1H)-one

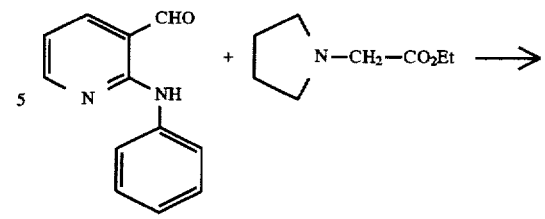

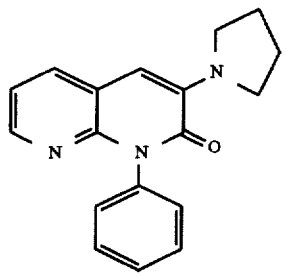

2-Phenylamino-3-pyridinecarboxaldehyde (2.0 g) and ethyl 2-pyrrolidinylacetate (1.65 g) were mixed together in dry tetrahydrofuran (THF) (5 mL) and t-butanol (1 mL) under N$_2$. To the mixture was added fresh potassium t-butoxide (KOt-Bu; 0.1 g). After 24 hr. a further 0.1 g of KOt-Bu was added, then at 25 hr and 48 hr. additional amounts of 0.1 g were added. After a total of 2.5 days an additional 0.436 g of KOt-Bu was added and the mixture was allowed to stir for a further 2.5 days. The solvent was removed and the residue was dissolved in CH$_2$Cl$_2$. Water was added and the pH of the aqueous layer was adjusted to about 7 with 1N-H$_2$SO$_4$. The organic layer was separated and chromatographed on silica gel. Fractions containing the product were combined and evaporated to an off-white crude product which was recrystallized from isopropanol to yield the desired product, m.p. 201.5°–202.5° C. Found, C, 74.23; H, 5.88; N, 14.30. Calcd. (for C$_{18}$H$_{17}$N$_3$O), C, 74.20; H, 5.88; N, 14.42

Example 2

Preparation of 3-(1-pyrrolidinyl)-1-(3-trifluoromethylphenyl)-1,8-naphthyridin-2(1H)-one

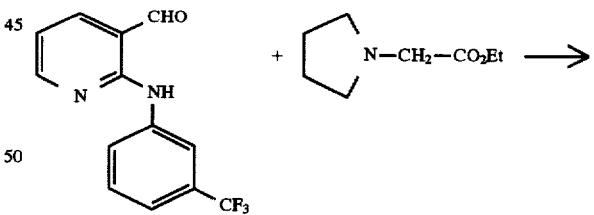

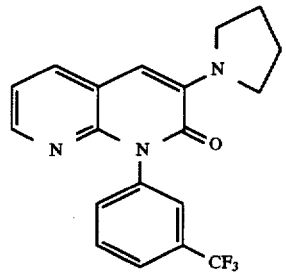

2-(3-Trifluoromethylphenyl)amino-3-pyridinecarboxaldehyde (1 g) and ethyl 2-pyrrolidinylacetate (0.6 g) were dissolved in a mixture of THF (10 mL)

and t-BuOH (2 mL). The solution was stirred under $N_2$ and to it was added fresh KOt-Bu (0.42 g). After 3 hr an additional 0.1 g of KOt-Bu was added, then after 4 hr the solvents were removed under vacuum. Water (10 mL) was added and the pH was adjusted to about 7 with $1N—H_2SO_4$. The product was extracted with 2×10 mL of $CH_2Cl_2$. The organic layer was washed with saturated NaCl solution (2×10 mL), dried ($Na_2SO_4$), and evaporated under vacuum. The product was purified by chromatography on silica gel and the light yellow product was then recrystallized from methanol to yield the desired product, mp 168.5°–170° C., after drying overnight under vacuum Found, C, 63.32; H, 4.22; N, 11.60; F, 16.28. Calcd. (for $C_{19}H_{16}N_3OF_3$), C, 63.50; H, 4.49; N, 11.69; F, 15.86.

By basically the same procedures as described above in Example 1 and 2, the following compounds were also prepared:

3-(1-Pyrrolidinyl)-1-(3-cyanophenyl)-1,8-naphthyridin-2-(1H)-one; mp >250° C.

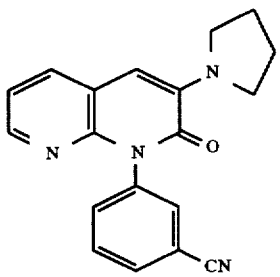

Found, C, 72.13; H, 5.06; N, 17.81. Calcd. (for $C_{19}H_{16}N_4O$), C, 72.13; H, 5.10; N, 17.71.

3-(4-Morpholinyl)-1-phenyl-1,8-naphthyridin-2(1H)-one; mp 167°–168° C.

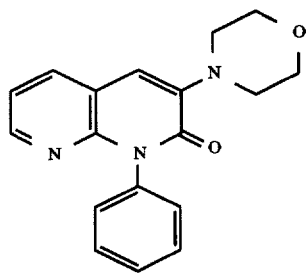

Found, C, 70.32; H, 5.55; N, 13.70. Calcd. (for $C_{18}H_{17}N_3O_2$), C, 70.34; H, 5.58; N, 13.67.

3-[3-(Hexahydro-1H-azepin-1-yl)-1,2-dihydro-2-oxo-1,8-naphthyridin-1-yl]-benzo-nitrile; mp 194°–196° C.

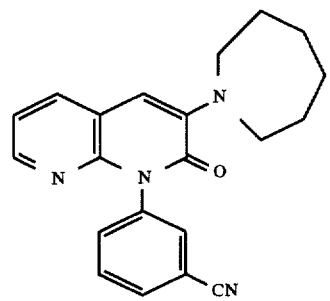

Found, C, 73.08; H, 5.57; N, 16.36. Calcd. (for $C_{21}H_{20}N_4O$), C, 73.23; H, 5.85; N, 16.27.

3-[1,2-Dihydro-3-(4-morpholinyl)-2-oxo-1,8-naphthyridin-1-yl]benzonitrile, mp 215°–217° C.

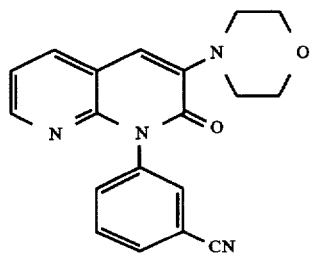

Found, C, 68.63; H, 4.73; N, 16.74. Calcd. C, 68.67; H, 4.85; N, 16.85.

The following formulations exemplify some of the dosage forms of the compositions of this invention. In each, the term "active compound" refers to 3-(4-morpholinyl)-1-phenyl-1,8-naphthyridin-2(1H)-one. However, this compound may be replaced by equally effective amounts of other compounds of formula I.

Example A

| | Tablets | | |
|---|---|---|---|
| No. | Ingredient | mg/tablet | mg/tablet |
| 1. | Active compound | 25 | 100 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 225 | 300 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No 4 and mix for 10–15 minutes. Add Item No. 5 and mix for 1–3 minutes. Compress the mixture to appropriate size and weigh on a suitable tablet machine.

Example B

| | Capsules | | |
|---|---|---|---|
| No. | Ingredient | mg/capsule | mg/capsule |
| 1. | Active compound | 25 | 100 |
| 2. | Lactose USP | 106 | 123 |
| 3. | Corn Starch, Food Grade | 40 | 70 |
| 4. | Magnesium Stearate NF | 4 | 7 |
| | Total | 175 | 300 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Example B

| | Capsules | | |
|---|---|---|---|
| No. | Ingredient | mg/capsule | mg/capsule |
| 1. | Active compound | 25 | 100 |
| 2. | Lactose USP | 106 | 123 |
| 3. | Corn Starch, Food Grade | 40 | 70 |
| 4. | Magnesium Stearate NF | 4 | 7 |
| | Total | 175 | 300 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

I claim:

1. A compound having the structural formula I

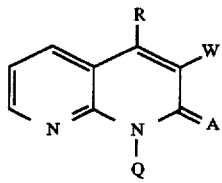

I or a pharmaceutically acceptable salt thereof, wherein:

A is O or S;

W represents

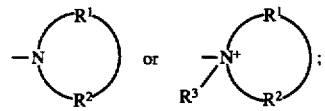

R represents H or $C_1$–$C_{10}$ alkyl;

$R^1$ represents $C_1$–$C_{10}$ alkanediyl;

$R^2$ represents a covalent bond or —($C_1$–$C_{10}$)alkanediyl-O—;

$R^3$ represents $C_1$–$C_{10}$ alkyl, $C_3$–$C_{10}$ cycloalkyl, benzyl, optionally substituted by 1–3 Y groups as defined below, or hydroxyalkyl having 2 to 6 carbon atoms between the N atom and the OH group;

Q represents phenyl, 1 - or 2-naphthyl, 1 -, 2-, 3-, 4-, 5-, 6- or 7-indenyl or 1-, 2-, 3-, 4-, 5-, 6- or 7-indanyl, each of which may optionally be substituted with 1 to 3 Y groups as defined below; and each Y is independently selected from $C_1$–$C_{10}$ alkyl, halo, nitro, $C_1$–$C_{10}$ alkoxy, $C_1$–$C_{10}$ alkylthio, —$CF_3$, —CN, $C_3$–$C_{10}$ cycloalkyl, $C_1$–$C_{10}$ alkylsulfinyl or $C_1$–$C_{10}$ alkylsulfonyl.

2. A compound according to claim 1, wherein W is the group

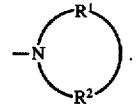

3. A compound according to claim 2, wherein A is O.

4. A compound according to claim 3, wherein R is H.

5. A compound according to claim 4, wherein Q is phenyl or substituted phenyl.

6. A compound according to claim 5, wherein W is

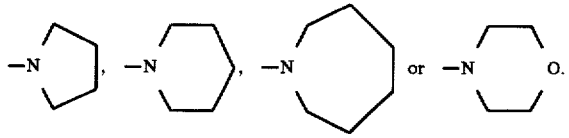

7. A compound according to claim 5, wherein W is

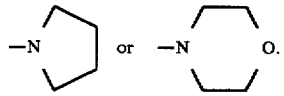

8. A compound according to claim 1, having the following structural formula:

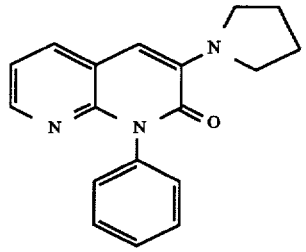

-continued
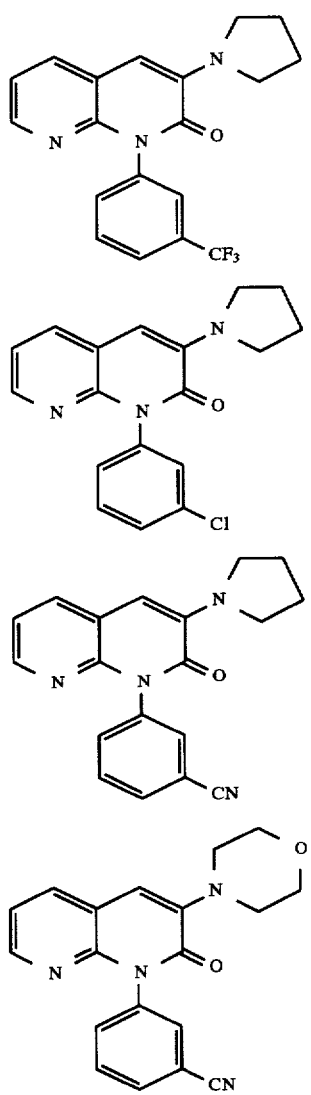
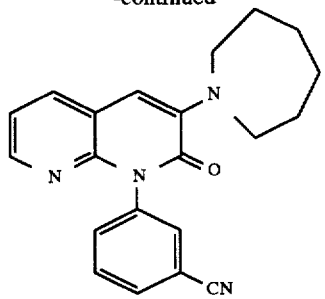
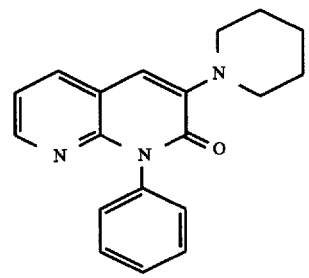
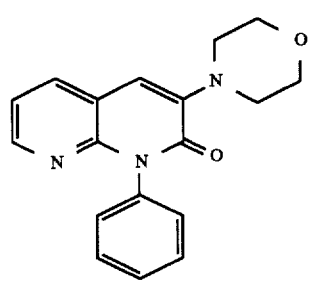
or a pharmaceutically acceptable salt thereof.
9. A pharmaceutical composition comprising a compound of formula I as defined in claim 1 in combination with a pharmaceutically acceptable carrier.
* * * * *